United States Patent
Agbaje et al.

(10) Patent No.: US 6,451,731 B1
(45) Date of Patent: Sep. 17, 2002

(54) STABLE CONCENTRATED PESTICIDAL SUSPENSION

(75) Inventors: Henry E. Agbaje, St. Louis, MO (US); Deborah H. Carter, Yakima, WA (US); Tracy A. Powers, Lee's Summit, MO (US); Shannon K. Hawkins, Dublin, OH (US); Alan J. Stern, Powell, OH (US); Shawn Zhu, Dublin, OH (US)

(73) Assignees: Monsanto Company, St. Louis, MO (US); CK Witco Corporation, Greenwich, CT (US)

( * ) Notice: Subject to any disclaimer, the term of this patent is extended or adjusted under 35 U.S.C. 154(b) by 0 days.

(21) Appl. No.: 09/652,146

(22) Filed: Aug. 31, 2000

Related U.S. Application Data

(60) Provisional application No. 60/266,299, filed on Sep. 10, 1999, and provisional application No. 60/221,297, filed on Jul. 27, 2000.

(51) Int. Cl.[7] ........................ A01N 25/04; A01N 37/36; A01N 57/02
(52) U.S. Cl. ........................ 504/118; 504/127; 504/148; 504/363; 504/364; 514/628; 514/937
(58) Field of Search .................... 504/127, 364, 504/118, 148, 363; 514/628, 937

(56) References Cited

U.S. PATENT DOCUMENTS

| 3,853,530 A | 12/1974 | Franz ........................ 71/76 |
| 5,078,782 A | 1/1992 | Nielsen et al. ................ 71/100 |
| 5,397,766 A | 3/1995 | Dexter ........................ 504/128 |
| 5,405,825 A | 4/1995 | Baker ........................ 504/139 |
| 5,543,383 A | 8/1996 | Parker et al. ................ 504/116 |
| 5,570,928 A | 11/1996 | Staunton et al. ............ 297/232 |
| 5,700,475 A | 12/1997 | Massman et al. ........... 424/408 |
| 5,888,935 A | 3/1999 | Fenderson et al. .......... 504/128 |

FOREIGN PATENT DOCUMENTS

| DE | 256 635 A1 | 5/1988 |
| EP | 0 024 188 A1 | 2/1981 |
| EP | 0 149 459 A2 | 7/1985 |
| EP | 0 243 872 A1 | 11/1987 |
| EP | 0 432 271 A1 | 6/1991 |
| EP | 0 433 577 A1 | 6/1991 |
| GB | 1 561 605 | 2/1980 |

*Primary Examiner*—S. Mark Clardy
(74) *Attorney, Agent, or Firm*—Senniger, Powers, Leavitt & Roedel; Joseph A. Schaper

(57) ABSTRACT

An emulsifiable pesticidal suspension concentrate composition is provided comprising (a) a pesticidally effective amount of a liquid pesticide of low solubility in water, for example a chloroacetamide herbicide such as acetochlor, (b) a pesticidally effective amount of a solid particulate pesticide, more particularly a salt-forming pesticide, for example a glyphosate herbicide, in solid particulate form, dispersed in the liquid pesticide, (c) a stabilizing amount of a suspension aid, (d) an emulsifying agent in an amount sufficient to emulsify the concentrate composition in a suitable volume of water to form a dilute sprayable composition, and (e) zero to an assay adjusting amount of an inert liquid in which the liquid pesticide is soluble or miscible. The concentrate composition is substantially non-aqueous. The liquid and solid pesticides are selected to be chemically compatible with each other. By substantial elimination of water and inert organic solvents according to the invention, suspension concentrate compositions can be provided having a very high concentration of active ingredients.

34 Claims, No Drawings

STABLE CONCENTRATED PESTICIDAL SUSPENSION

CROSS REFERENCE TO RELATED PATENT APPLICATIONS

This patent claims the benefit of U.S. Provisional Patent Application Serial Nos. 60/266,299, filed Sep. 10, 1999, now abandoned, and No. 60/221,297, filed Jul. 27, 2000, now abandoned. The complete text of these provisional patent applications is incorporated herein by reference.

FIELD OF THE INVENTION

The present invention relates to pesticidal compositions useful in agriculture and related industries. More specifically, the present invention relates to concentrated pesticidal compositions containing a solid pesticide and a liquid pesticide, and to a method of killing or controlling unwanted life forms using such compositions.

BACKGROUND OF THE INVENTION

Solid pesticides are commonly formulated as emulsifiable suspension concentrates, wherein typically a pesticidally active ingredient in a solid particulate state is suspended in a non-active liquid carrier. The liquid carrier in such concentrates can be aqueous or non-aqueous, for example a hydrocarbon oil or other organic liquid, and is selected such that the solid pesticide has low solubility in the liquid carrier. Most solid pesticides are of low solubility in water and can be formulated as aqueous suspension concentrates, or as non-aqueous suspension concentrates wherein the liquid carrier is not an effective solvent for the pesticide.

Suspension concentrate formulations preferably have a high concentration of active ingredient, have good storage stability, and are easy to use. In particular, because these concentrates are typically diluted with water at the time of use, they must be readily emulsified in water, and have good emulsion stability in the diluted state.

Physical stability of suspension concentrates, both during storage and during use, is of particular concern with these formulations having a solid particulate phase and a continuous liquid phase. Suspension concentrates are inherently unstable in a gravitational field because of difference in density between the solid pesticide and the liquid carrier, which can result in separation of the formulation over time into a pesticide-rich layer and a carrier-rich layer. In extreme cases, phase separation occurs, wherein the solid particulate pesticide, typically the denser phase, settles at the bottom of the liquid phase. It is therefore generally necessary to include one or more suspension aid(s) in the formulation to assist in maintaining suspension of the solid and thereby improve the physical stability. If separation occurs, it is preferred that the solid can be readily resuspended with minimum agitation of the formulation.

Further, a pesticidal suspension concentrate to be used in the agricultural industry is typically diluted with water to prepare a dilute sprayable composition which is then applied by spraying to soil and/or plants in a field, for example by means of conventional spraying equipment. At the time of use, therefore, it is desirable that the suspension concentrate is readily emulsified in water, with no more than a minimal and acceptable amount of segregation of components into distinct layers referred to in the industry as "creaming", and/or no more than a minimal and acceptable amount of sedimentation. In order to accomplish this, one or more surfactants or emulsifiers are therefore also typically included in suspension concentrates to improve dispersibility in water.

Suspension concentrates having an oil as the liquid carrier are particularly troublesome and require an emulsifier that is capable, by a process of emulsification, of dispersing the oil without forming gels or lumps, and distributing the pesticide in the aqueous phase of a dilute sprayable composition. This emulsification must take place quickly, without complications.

A number of pesticides, including for example some highly popular and effective herbicidal agents that are especially useful for controlling undesirable plant species by post-emergence application, are routinely supplied as water-soluble salts in aqueous solution. Unless converted to a more lipophilic form, for example alkyl esters, such pesticides are generally very poorly soluble in non-aqueous carriers such as organic solvents and oils. Examples of such salt-forming pesticides include the herbicide N-phosphonomethylglycine, also known as glyphosate, DL-homoalanin-4-yl(methyl)phosphinic acid, also known as glufosinate, and several herbicides of the imidazolinone class, such as 2-(4-isopropyl-4-methyl-5-oxo-2-imidazolin-2-yl)nicotinic acid, also known as imazapyr.

U.S. Pat. No. 5,078,782 to Nielsen & Månsson describes a suspension concentrate composition comprising a solid particulate pesticide, for example a herbicide such as phenmedipham or glyphosate, suspended in an oily carrier, for example a refined paraffinic oil having 0–17% aromatic content, with one or more surfactants. Also described is a suspension concentrate having phenmedipham in suspension and the herbicide triallate in solution in the oily carrier. The content of the oily component in the composition as a whole is said to be 20–90% by weight.

U.S. Pat. No. 5,397,766 to Dexter describes an emulsifiable suspension concentrate composition comprising solid particulate glyphosate and/or an imidazolinylnicotinic acid, e.g., imazapyr, in the acid form thereof, dispersed in a water-immiscible inert liquid carrier such as a non-paraffinic aromatic solvent. The composition is said to further comprise an anionic surfactant and a nonionic surfactant, and optionally an antifoam agent and a suspending or thickening agent.

The great majority of pesticides, for example herbicides, are of very low solubility in water and are not convertible to water-soluble salts. Many of these pesticides are readily soluble in organic solvents and are typically formulated as emulsifiable concentrates comprising a solution of pesticide in an organic solvent carrier, together with one or more surfactants as emulsifiers to facilitate emulsification on preparation by the end-user of a dilute aqueous sprayable composition.

A relatively small number of pesticides are liquid at ambient temperatures, having a melting point lower than about 15° C. Such pesticides illustratively include the pre-emergence chloroacetamide herbicides 2-chloro-N-(ethoxymethyl)-N-(2-ethyl-6-methylphenyl)acetamide, also known as acetochlor, and 2-chloro-N-(2-ethyl-6-methylphenyl)-N-(2-methoxy-1-methylethyl)acetamide, also known as metolachlor, and can optionally be formulated as emulsifiable concentrates with only a minimal amount of an organic solvent, or none at all.

It is frequently desired in the art to coformulate as a liquid concentrate a salt-forming pesticide with a pesticide having low solubility in water, herein referred to for convenience as a "water-insoluble" pesticide. For example, a combination of a salt-forming post-emergence herbicide such as glyphosate or glufosinate with a water-insoluble pre-emergence herbicide, for example a chloroacetamide herbicide such as acetochlor or metolachlor, is useful for killing or controlling already emerged weeds and for providing residual control of weeds that would otherwise later emerge.

Roundup® Ultra herbicide of Monsanto, which contains as active ingredient glyphosate in the form of its isopropylammonium salt, is labeled by the manufacturer for use in tank-mixture with Dual® and Dual® II herbicides of Novartis, which contain as active ingredient metolachlor, Frontier® herbicide of BASF, which contains as active ingredient the chloroacetamide herbicide dimethenamid, and Harness® herbicide of Monsanto and Surpass® and TopNotch® herbicides of Zeneca, which contain as active ingredient acetochlor.

It is often of benefit to provide a single concentrate composition containing both a salt-forming pesticide and a water-insoluble liquid pesticide, for example glyphosate and acetochlor respectively. Typically this has been accomplished by providing a concentrated emulsion, for example an oil-in-water emulsion, wherein the salt-forming pesticide is present, usually in the form of a water-soluble salt, in an aqueous phase and the water-insoluble pesticide is present in an oil phase. The herbicidal product FieldMaster® of Monsanto contains glyphosate in the form of its isopropylammonium salt in the aqueous phase and acetochlor in the oil phase; also present in this product is a third herbicide, atrazine, dispersed in the aqueous phase as a solid particulate material.

Liquid concentrate formulations are also known wherein a solid particulate pesticide of low solubility in water is suspended in an aqueous phase and a second water-insoluble pesticide is present in an oil phase dispersed in the aqueous phase. Such formulations possess characteristics both of emulsions and suspensions and are known in the art as suspoemulsions. An example is the FieldMaster® product described above, but more commonly there is no salt-forming pesticide present in the aqueous phase. Harness® Xtra herbicide of Monsanto is a suspoemulsion formulation having solid particulate atrazine suspended in the aqueous phase and acetochlor in the oil phase of the suspoemulsion.

Concentrated emulsion and suspoemulsion formulations have many attractive features but have a disadvantage that the concentration of active ingredients tends to be limited, because of the significant volume of water that must be present as a solvent for a salt-forming pesticide and/or as a suspension medium for the solid particulate pesticide, and to provide a stable emulsion.

U.S. Pat. No. 5,700,475 to Massman & Miller discloses a "simple premix" of the water-insoluble solid herbicide halosulfuron and an emulsifiable concentrate containing 82.45% acetochlor. The halosulfuron and the acetochlor emulsifiable concentrate were found to be chemically reactive with each other, leading to degradation of the halosulfuron, and this problem was overcome by microencapsulation of the halosulfuron prior to mixing with the acetochlor emulsifiable concentrate.

There remains a need in the pesticide industry to supply stable liquid concentrate pesticidal formulations which have a high concentration of two or more chemically compatible active ingredients, one of which is liquid at ambient temperatures. This need is particularly acute where the second active ingredient is a salt-forming pesticide that is normally formulated as a water-soluble salt.

SUMMARY OF THE INVENTION

The present invention contemplates a formulation that satisfies the need described immediately above by substantially eliminating the requirement for an inert carrier liquid such as water or an organic solvent. Accordingly there is now provided an emulsifiable pesticidal suspension concentrate composition comprising (a) a pesticidally effective amount of a liquid pesticide of low solubility in water, (b) a pesticidally effective amount of a solid particulate pesticide, more particularly a salt-forming pesticide in solid particulate form, dispersed in the liquid pesticide, (c) a stabilizing amount of a suspension aid, (d) an emulsifying agent in an amount sufficient to emulsify the concentrate composition in a suitable volume of water to form a dilute sprayable composition, and (e) zero to an assay adjusting amount of an inert liquid in which the liquid pesticide is soluble or miscible. The concentrate composition is substantially non-aqueous. The liquid and solid pesticides are selected to be chemically compatible with each other.

It will be recognized that in manufacturing practice it may be difficult to eliminate the inert liquid altogether. This is because at a final stage in any manufacturing process for a concentrate formulation it is generally necessary to add a small amount of an inert material to adjust the active ingredient assay of the formulation to the precise required specifications. An assay adjusting amount of an inert liquid herein is no more than about 10% by weight of the concentrate composition, and in most cases it will be found that considerably less than 10% is needed, typically no more than about 5% by weight.

By "substantially non-aqueous" herein is meant that substantially no water is included in the concentrate composition except for small amounts of water that can incidentally be introduced in raw materials during preparation of the concentrate composition. For example, certain surfactants useful as emulsifying agents can contain small amounts of water. Also, where the solid particulate pesticide is water-soluble, it can be difficult, and is unnecessary, to remove all traces of water from the solid particulate pesticide prior to preparation of the concentrate composition. It will further be understood that addition of a small amount of water, for example up to about 10% by weight of a composition, will not remove the composition from the scope of the present invention so long as all features set out above remain in effect.

By "chemically compatible" herein is meant that neither the solid nor the liquid pesticide exhibits a significantly increased rate of chemical degradation due to admixture with the other pesticide.

By substantial elimination of water and inert organic solvents, suspension concentrate compositions can be provided having a concentration of active ingredients of about 40% to about 97% by weight, preferably about 60% to about 90% by weight, of the composition.

DETAILED DESCRIPTION OF PREFERRED EMBODIMENTS

A pesticide as defined herein includes any chemical classified as a pesticide by any regulatory authority; for example in the United States by the Environmental Protection Agency (EPA). Generally, a pesticide is a chemical which, when applied in a pesticidally sufficient amount to a susceptible plant, animal and/or microorganism and/or to the locus thereof, kills or inhibits the growth of the plant, animal and/or microorganism. Included non-restrictively among pesticides are herbicides, fingicides, insecticides, acaricides, nematicides, molluscicides and plant and insect growth regulators.

In a composition of the present invention, at least one pesticide, more particularly at least one salt-forming pesticide, is suspended in solid particulate form in at least one liquid pesticide. The composition may contain any combination of such liquid and solid pesticides provided there is at least one liquid and at least one solid active ingredient. The liquid pesticide, in addition to providing its customary pesticidal activity, operates as the carrier for the solid pesticide, replacing inert aqueous or non-aqueous carrier liquids hitherto employed. The term "inert" as used herein applies to an ingredient not itself having pesticidal activity in the amounts present in the composition.

Solid pesticides useful herein do not melt at temperatures below about 60° C. Preferably, the solid pesticide has a solubility not greater than about 10% by weight, ore preferably not greater than about 5% by weight, and most preferably not greater than about 1% by weight, in the liquid pesticide. It is acceptable that the liquid pesticide solubilizes a small amount of solid pesticide but this is preferably kept to a minimum. It is desirable that the liquid pesticide suspends the solid without forming a solution.

Whether or not a solid can be dissolved in a liquid is determined by the interaction forces (1) between the pure solid molecules, (2) between the pure liquid molecules, and (3) between solid molecules and liquid molecules. Solubility parameter, a measure of the intermolecular forces in pure substances, is useful in determining the solubility of a solid in a liquid. Solids and liquids with comparable solubility parameters have similar interaction forces. Therefore, a solid will have high solubility in a liquid if the solubility parameters of the solid and the liquid are comparable.

Solubility parameter is the square root of cohesive energy density. The cohesive energy can be calculated from the enthalpy of vaporization $\Delta H_v$ and the work that is required to expand the vapor against the atmosphere (volume work). The cohesive energy per unit volume, i.e., the cohesive energy density, is defined as:

$$e=(\Delta H_v-RT)/V$$

where R is the gas constant, T is the temperature and V is the volume.

Solubility parameters can be calculated or determined by routine experimentation as is known in the art. For example, solubility parameters for a solid-liquid system can be determined by use of Flory temperature, which is the temperature at which the solid-liquid system has no interaction. At such a temperature, the solubility parameters for both the solid and the liquid are the same and the solid is soluble in the liquid. When the Flory temperature is much higher than room temperature, the solid will not be soluble in the liquid at room temperature. Generally, a difference of about 5 (J cm$^3$)$^{1/2}$ between the solubility parameters of the solid and liquid will result in the solid being insoluble in the liquid. For further discussion regarding solubility parameters, see Krevelene, *Properties of Polymer, Correlations with Chemical Structures*, and Barton, *Handbook of Solubility Parameters and Other Cohesion Parameters*.

Appropriate pairs of liquid and solid pesticides can be selected such that the solid does not dissolve in the liquid by ensuring that the solubility parameters of the liquid and solid are dissimilar. Generally speaking, a solid from the same chemical family as the liquid is less likely to have high solubility in the liquid, and accordingly it is usually preferable to select solid and liquid pesticides from different chemical families.

After a solid/liquid pair has been selected, it is desirable to confirm the solubility of the solid in the liquid by routine experiment.

Liquid pesticides useful herein preferably have a melting point lower than about 15° C., more preferably lower than about 0° C. In a presently preferred embodiment, the liquid pesticide is a herbicide. Liquid herbicides useful herein include but are not limited to acrolein; aryloxyphenoxy herbicides, e.g. fluazifop-butyl and fluazifop-P-butyl; chloroacetamides, e.g., acetochlor, butachlor, dichlormid, dimethenamid, metolachlor and pretilachlor; cinmethylin; cyclohexanediones, e.g., clethodim and sethoxydim; dinitroanilines, e.g., isopropalin; esters of phenoxy herbicides, e.g., 2,4-D isooctyl ester; and thiocarbamates, e.g., butylate, cycloate, EPTC, ethiolate, molinate, pebulate, thiobencarb and vemolate.

In another embodiment, the liquid pesticide is an insecticide. Liquid insecticides useful herein include but are not limited to organophosphorus insecticides, e.g., diazinon, fonofos, malathion and parathion; and pyrethroids, e.g., allethrin and zeta-cypermethrin.

In another embodiment, the liquid pesticide is a fungicide. Liquid fungicides useful herein include but are not limited to etridiazole; imidazoles, e.g. pefurazoate; morpholines, e.g., fenpropidin, fenpropimorph and tridemorph; piperalin; pyrifenox; and triazoles, e.g., propiconazole.

The solid pesticide can be a herbicide. Solid herbicides include without limitation amides, e.g., mefluidide, isoxaben, napropamide, propanil and propyzamide; bentazone; carbamates, e.g., desmedipham and phenmedipham; chloroacetamides, e.g., propachlor; chlorthal-dimethyl; dichlobenil; dinitroanilines, e.g., benfluralin, oryzalin, pendimethalin and prodiamine; diphenylethers, e.g., bifenox, fomesafen and oxyfluorfen; fluthiacet-methyl; oxadiazon; pyridazinones, e.g., chloridazon and norflurazon; pyridines, e.g., dithiopyr and thiazopyr; pyridinones, e.g., fluridone; triazines and triazinones, e.g., ametryn, atrazine, cyanazine, hexazinone, metribuzin, prometon, prometryn and simazine; triazolopyrimidines, e.g., flumetsulam; uracils, e.g., bromacil and terbacil; ureas e.g., diuron, fluometuron, linuron, siduron and tebuthiuron; and salt-forming herbicides.

Preferred solid herbicides useful herein as the solid pesticide are salt-forming herbicides. Salt-forming herbicides include but are not limited to amitrole; aryloxyphenoxypropionates, e.g., diclofop, fenoxaprop, fluazifop, haloxyfop, quizalofop and quizalofop-P; asulam; benazolin; benzoic acids, e.g., chloramben, chlorthal, dicamba, naptalam and 2,3,6-TBA; bipyridyls, e.g., diquat, paraquat; carfentrazone; difenzoquat; diphenylethers, e.g., acifluorfen and fluoroglycofen; fatty acids, e.g., nonanoic acid; flumiclorac; fluthiacet; fosamine; glufosinate; glyphosate; hydroxybenzonitriles, e.g., bromoxynil and ioxynil; imidazolinones, e.g., imazamethabenz, imazamox, imazapic, imazapyr, imazaquin and imazethapyr; maleic hydrazide; metam; organoarsenicals, e.g., dimethylarsinic acid and methylarsonic acid; phenoxyalkanoic acids, e.g., 2,4-D, 2,4-DB, dichlorprop, MCPA, MCPB and mecoprop; pyridinecarboxylic acids, e.g., clopyralid, picloram and triclopyr; quinolinecarboxylic acids, e.g., quinclorac and quinmerac; and sulfamic acid.

Salt-forming herbicides and other salt-forming pesticides can be acids or bases and can be present in the composition in their acid or base form, or in the form of an agriculturally acceptable salt. Salt-forming pesticides that are acids can illustratively be present in the form of a salt selected from alkali metal, e.g., potassium and sodium, salts, ammonium salt, organic ammonium, e.g., dimethylammonium, isopropylammonium and ethanolarnmonium, salts, organic sulfonium, e.g., trimethylsulfonium, salts, and mixtures thereof. Salt-forming pesticides that are bases can illustratively be present in the form of a salt selected from halide, e.g., chloride, bromide and iodide, salts, carboxylate, e.g., acetate, propionate, succinate, lactate, citrate and tartrate, salts, sulfate salts, ethosulfate salts, phosphate salts, and mixtures thereof.

The solid pesticide can be an insecticide. Solid insecticides include but are not limited to carbamates, e.g., aldicarb, carbaryl and methomyl; organochlorine insecticides, e.g., endosulfan; organophosphorus insecticides, e.g., acephate and dimethoate; and pyrethroids, e.g., bifenthrin and tefluthrin.

The solid pesticide can be a fingicide. Solid fungicides useful herein include but are not limited to benzimidazoles, e.g., benomyl and carbendazim; captan; chlorophenyls, e.g., chlorothalonil and quintozene; dicarboximides, e.g., iprodione; dithiocarbamates, e.g., mancozeb, maneb, thiram and zineb; inorganic fungicides, e.g., sulfur, copper hydroxide, copper oxychloride and mercurous chloride; morpholines, e.g., dimethomorph; phenylamides, e.g., metalaxyl; piperazines, e.g., triforine; pyrimidines, e.g., fenarimol; strobilurins, e.g., azoxystrobin; and triazoles, e.g., diniconazole.

In a preferred embodiment, the liquid pesticide is a chloroacetamide herbicide, for example one selected from acetochlor, butachlor, dichlormid, dimethenamid, metolachlor and pretilachlor, more preferably from acetochlor and metolachlor; and the solid pesticide is a salt-forming herbicide selected from glyphosate, glufosinate and salts thereof, more preferably from glyphosate and salts thereof.

In certain embodiments, including an embodiment where the liquid pesticide is a chloroacetamide herbicide, a safener can optionally be added to the formulation to reduce risk of injury to a crop such as corn. For example, formulations of the invention containing acetochlor or metolachlor can optionally further comprise a safener, in a safening effective amount, selected from benoxacor, fenclorim, flurazole, fluxofenim, furilazole and oxabetrinil. Presently preferred safeners are benoxacor and furilazole. Benoxacor is especially preferred where the composition contains metolachlor, and furilazole is especially preferred where the composition contains acetochlor.

It will be understood that a suspension concentrate composition of the invention can contain more than one liquid herbicide and/or more than one solid particulate herbicide.

A major benefit of suspension concentrate compositions of the invention is that they enable very high loading, or concentration, of pesticidal active ingredients. Accordingly, the total amount of pesticide in a suspension concentrate of the invention is typically 40% by weight or greater. Preferably, the amount of total pesticide, expressed in the case of a salt-forming pesticide such as glyphosate and glufosinate as acid equivalent, in the suspension concentrate is about 40% to about 97% by weight, more preferably about 50% to about 95% by weight, even more preferably about 60% to about 90% by weight, and most preferably about 65% to bout 85% by weight.

Preferably the weight ratio of total solid pesticide, expressed where appropriate as acid equivalent, to total liquid pesticide is about 1:9 to about 2:1. Particularly where the solid pesticide is glyphosate or glufosinate or a salt thereof and the liquid pesticide is acetochlor or metolachlor, a suitable weight ratio of solid pesticide, expressed as acid equivalent, to liquid pesticide is about 1:6 to about 1:1, more preferably about 1:5 to about 1:1, even more preferably about 1:4 to about 1:1, for example about 1:3 to about 1:2.

When selecting pesticidal active ingredients for a composition of the invention, it is desirable to determine chemical and biological compatibility of the active ingredients. It is also desirable to select a pesticide combination in which the individual pesticides have complementary or synergistic effects. For instance, the following general rules may be utilized as guidelines in selection of pesticide combinations: (1) a fungicide should generally not be used in combination with a herbicide or plant growth inhibitor; (2) a herbicide or growth inhibitor effective predominantly on dicotyledonous, e.g., broadleaf, plants can often be usefully combined with one effective predominantly on monocotyledonous, e.g., grass, plants; (3) a herbicide having predominantly pre-emergence or residual activity can often be usefully combined with one having predominantly post-emergence or foliar activity; and (4) an insecticide can generally be used in combination with a herbicide, plant growth inhibitor or fungicide.

The present invention has been found to have particular applicability for a combination of a pre-emergence herbicide with a post-emergence herbicide, where the former has residual activity when applied to soil and the latter has contact and/or systemic activity when applied to foliage. Application of such a combination of herbicides to a field having weeds already emerged and weeds not yet emerged gives particularly effective and economic weed control. For example, a combination of acetochlor as the pre-emergence herbicide and glyphosate or a salt thereof as the post-emergence herbicide is especially well suited to formulation according to the present invention. In such a combination, acetochlor is a suitable liquid herbicide wherein glyphosate or a salt thereof can be suspended in solid particulate form.

Not all glyphosate salts are readily prepared in solid particulate form. Among he most convenient forms of glyphosate for use according to the invention are glyphosate acid and the ammonium and sodium salts of glyphosate, although other salts can be used if desired. Particularly favorable results have been obtained with the ammonium salt of glyphosate.

A composition of the invention contains a stabilizing amount of a suspension aid. The suspension aid improves physical stability by maintaining a stable suspension of the solid particulate pesticide in the liquid pesticide. Compositions prepared without a suspension aid typically exhibit separation into two layers, one enriched in the liquid pesticide and one enriched in the solid particulate pesticide, in a few days or even less.

Preferred suspension aids useful herein are those capable of providing thixotropic or shear thinning characteristics. Preferably a suspension concentrate of the invention has a thixotropic index of at least 2.5, more preferably at least 3.0, at a viscosity ratio of 3 to 30 rpm, as measured using a Brookfield Viscometer model LVT DV II with a no. 4 spindle at room temperature.

The suspension aid preferably comprises a silica, more preferably a hydrophilic fumed or precipitated silica. A silica useful as a suspension aid herein preferably has a BET surface area of about 100 to about 300 $m^2/g$, more preferably about 120 to about 250 $m^2/g$ and most preferably about 150 to about 250 $m^2/g$, and a bulk density of about 10 to about 70 g/l, more preferably about 20 to about 50 g/l.

The suspension aid should be selected so as to provide less than about 2% separation of the liquid and solid pesticides in 2 weeks at room temperature, and less than about 5% separation in 4 weeks at room temperature. If separation should occur in a composition of the invention, the particles are easily resuspended by utilizing a minimum of agitation.

Specific examples of preferred silicas include Aerosil® 200, an amorphous hydrophilic fumed silica of Degussa Corporation, and Hi-Sil® T-152, an untreated amorphous precipitated silica of PPG Industries. Aerosil® 200 has a surface area of 175–225 m²/g and a bulk density of about 30 g/l. Hi-Sil® T-152 has a surface area of about 150 m²/g and a bulk density of about 48 g/l.

Preferably, silica is used in an amount of about 0.05% to about 5%, more referably about 0.2% to about 3%, and most preferably about 0.5% to about 2%, by eight of the suspension concentrate composition.

A composition of the invention contains an emulsifying agent in an amount sufficient to emulsify the concentrate composition in a suitable volume of water to form a dilute sprayable composition. Emulsifying agents are typically surfactants or wetting agents. Surfactants used as emulsifying agents in a composition of the invention can also serve other useful functions, for example in aiding dispersion of the concentrate composition when it is added to water, and/or as an enhancer of biological activity, particularly of a pesticide such as the herbicide glyphosate having postemergence activity by application to foliage.

Suitable surfactants or wetting agents can be selected from those conventional in the art, for example those described in U.S. Pat. No. 3,853,530 to Franz, U.S. Pat. No. 5,543,383 to Parker & Holejko, or above-cited U.S. Pat. No. 5,078,782 or U.S. Pat. No. 5,397,766. Surfactants useful as emulsifying agents in contemplated compositions include nonionic, cationic, anionic, amphoteric, zwitterionic and polymeric surfactants and mixtures thereof. Such surfactants typically have a hydrophobic moiety that is hydrocarbon based, organosilicone based or fluorocarbon based.

Useful classes of surfactant include without restriction block copolymers of ethylene oxide and propylene oxide or butylene oxide; alkylaryl alkoxylates, especially ethoxylates and propoxylates, for example ($C_{8-12}$ alkyl)phenol ethoxylates; tertiary ($C_{8-22}$ alkyl)amine and ($C_{8-22}$ alkyl) etheramine alkoxylates, especially ethoxylates; quaternary ($C_{8-22}$ alkyl)ammonium and ($C_{8-22}$ alkyl)etherammonium salts and alkoxylates, especially ethoxylates, thereof; fatty acid alkoxylate, especially ethoxylate, esters; fatty alcohol alkoxylates, especially ethoxylates (alkylether surfactants); alkylsulfonates; alkylbenzene and alkylnaphthalene sulfonates; sulfated fatty alcohols and alkylether sulfates, sulfated amines and acid amides; long-chain acid esters of sodium isethionate; esters of sodium sulfosuccinate; sulfated and sulfonated fatty acid esters; petroleum sulfonates; N-acyl sarcosinates; alkyl polyglycosides; sorbitan esters; and phosphate esters of fatty alcohols and fatty alcohol alkoxylates.

Specific illustrative examples of useful surfactants include Witconate® 1298-HA, a branched dodecylbenzene sulfonic acid; Witcamine® TAM-105, a allowamine ethoxylate; Witconol® SN-120, an alcohol ethoxylate; Sponto® AL69-66, a sorbitol tallate ethoxylate; Witconate® P-1059, an isopropylammonium salt of dodecylbenzene sulfonate; and Witconol® NS-500-LQ, a butanol EO/PO copolymer; all available from Crompton Corporation.

Organosilicone surfactants useful herein illustratively include silicone polyalkylene oxide copolymers such as Silwet® L-77 and Silwet® 408 of Crompton Corporation. Blends of organosilicone surfactants with hydrocarbon based surfactants can be used.

Particularly preferred surfactants include ethylene oxide/ propylene oxide (EO/PO) block copolymers, alkylamine ethoxylates, fatty alcohol alkoxylates, alkyl benzene sulfonates, sorbitol ethoxylates and vegetable oil ethoxylates.

Particularly where the solid particulate pesticide is glyphosate or a salt thereof, it is preferred to include at least one surfactant that enhances glyphosate herbicidal activity in plants, for example by improving retention of the herbicide on, or absorption of the herbicide into, foliage of the plants.

Such a surfactant can illustratively be selected from alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene N-methyl alkylammonium salts, polyoxyethylene N-methyl alkyletherammonium salts, alkyldimethylamine oxides, polyoxyethylene alkylamine oxides, polyoxyethylene alkyletheramine oxides, alkylbetaines and alkylamidopropylamines, where the average number of oxyethylene units, if present, per surfactant molecule is no greater than about 50, and the average number of glucose units, if present, per surfactant molecule is no greater than about 2. The term "alkyl" as used in this paragraph reflects common usage in the art and means $C_{8-12}$ aliphatic, saturated or unsaturated, linear or branched hydrocarbyl.

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Preferably, the total amount of surfactant present is about 3% to about 60% by weight, more preferably about 5% to about 40% by weight, even more preferably about 8% to about 20% by weight, and most preferably about 10% to about 15% by weight of the suspension concentrate.

Compositions of the present invention contain no more than an assay adjusting amount of an inert liquid in which the liquid pesticide is soluble or miscible. Such inert liquids, including mineral, vegetable and silicone oils and organic solvents, e.g., paraffinic and olefinic hydrocarbons, aromatic solvents, ketones, alcohols, glycols, glycol ethers, fatty acids, lower alkylesters of oils and fatty acids, etc., can be present in relatively small amounts of less than about 10% by weight of a composition without substantially affecting the properties of the composition. Preferably the amount of such inert liquids is less than about 5% by weight, more preferably less than about 2% by weight, of the composition.

It is advantageous to have a relatively solvent-free composition due to the flammability of most solvents. Further, substantial elimination of an inert liquid carrier enables an increase in concentration of active ingredients.

Preferably, a composition of the present invention has a viscosity at 25° C. of about 400 cPs to about 7000 cPs, more preferably about 800 cPs to about 5000 cPs, and most preferably about 1500 cPs to about 3000 cPs. These viscosity ranges relate to measurements made using a Brookfield Viscometer, Model LVT DV II, at 30 rpm with a spindle selected appropriate to the viscosity range; as will be understood by those of skill in the art, other types of viscosity measuring equipment and other conditions can give very different viscosity readings with the same composition. However measured, the viscosity should be low enough to ensure good pouring and dispersing properties, yet high enough so that the suspension has sufficient stability.

Suspension aids such as silicas, or standard thickeners such as Attagel™ 50 typically used in oil-based systems, may be optionally used to increase viscosity of the pesticide concentrate.

An illustrative herbicidal suspension concentrate of the invention contains at least one liquid herbicide, for example acetochlor, having suspended therein in solid particulate form a herbicide selected from glyphosate acid and the sodium and ammonium salts of glyphosate, together with about 5% to about 15% by weight of at least one alkylamine ethoxylate surfactant, about 1% to about 10% by weight of at least one EO/PO block copolymer, for example a butanol EO/PO block copolymer, about 1% to about 10% of at least one additional nonionic surfactant, about 1% to about 10% of at least one sulfonic acid or sulfonate surfactant, and about 0.5% to about 5% by weight of at least one silica. This illustrative composition has a total herbicide concentration of about 65% to about 85% by weight, and has a weight ratio of glyphosate, expressed as acid equivalent, to the liquid herbicide of about 1:5 to about 1:1.

Suspension concentrates of the present invention are employed in a simple manner by diluting the concentrate with a suitable amount of water to form a dilute composition, stirring or agitating the dilute composition for a short time, and then applying it to a field or plant. Typically, one part by volume of a suspension concentrate is diluted with about 20 to about 1000 parts by volume of water. Preferred suspension concentrates of the invention are easily emulsified in water with agitation kept to a minimum. Once diluted, the composition is then applied to a targeted surface typically by means of spraying, for example through use of conventional spraying equipment.

In one embodiment, a diluted composition of the invention containing an acetochlor or metolachlor herbicide as the liquid pesticide and a glyphosate or glufosinate herbicide as the solid particulate pesticide is applied to a field prior to planting of a crop therein, the field having emerged weeds. The glyphosate or glufosinate is effective in killing or controlling these emerged weeds, while the acetochlor or metolachlor is effective in controlling weeds not yet emerged and/or in preventing their emergence. Particularly where the crop to be planted is corn, it is generally preferred to include a safener for the acetochlor or metolachlor herbicide, such as benoxacor or furilazole, in the composition.

In another embodiment, a similar diluted composition of the invention is applied to a field after planting of a crop therein, and preferably after emergence of the crop, the field having emerged weeds. Where the field is to be sprayed post-emergence of the crop, it is important that the crop variety selected be one that is tolerant of the glyphosate or glufosinate herbicide. Such varieties can originate by conventional plant breeding techniques or by genetic transformation. For example, corn seeds genetically modified to tolerate glyphosate herbicides are available under the trademark Roundup Ready®. For application post-emergence of the crop, the presence of a safener for the acetochlor or metolachlor herbicide may not be necessary.

EXAMPLES

The following Examples are provided for illustrative purposes only and are not to be interpreted as limiting the scope of the present invention. The Examples will permit better understanding of the invention and better perception of its advantages.

In the following illustrative Examples, test methods for various parameters were as follows.

In Examples 1–6, viscosity was measured at the temperature indicated using a Brookfield Viscometer Model LVT DV II at various rotational speeds using a no. 4 spindle. In Examples 15–17, viscosity was measured at the temperature indicated using a Haake RV20 viscometer at a shear rate of 45 sec$^{-1}$.

Physical stability of a suspension concentrate composition was measured at room temperature by visual observation of the appearance of the composition over a 4-week period of storage at ambient temperature. The amount of oil forming a clear phase on the top of the composition was measured after 2, 3 and 4 weeks. A composition was considered to have acceptable physical stability if such a clear oily phase constituted less than about 2% of the total volume of the composition in 2 weeks, or less than about 5% of the total volume of the composition in 4 weeks.

Bloom (or spontaneity) of a composition was rated by visual observation of the ease with which emulsion formation, i.e., formation of a white cloud, occurs upon dilution in water. In a cylinder without agitation, 5 ml of the composition was added to 95 ml of water of known hardness rating. The formation of the white cloud was then observed while inverting the cylinder by hand. The composition was rated on ease of forming an emulsion as excellent, good, fair or poor.

Emulsion stability was rated after bloom observation by inverting the cylinder ten times and then allowing it to rest undisturbed. Visual observation of the amount of cream or sediment was made at specified time intervals of 30 minutes, 1 hour, 2 hours, and overnight. Emulsion stability of a composition wherein, after overnight standing, cream amounted to no more than 1% of the total volume of the dilute emulsion, was rated excellent. Where cream amounted to 1–2% of total volume, emulsion stability was rated good. Where cream amounted to 2–4% of total volume, emulsion stability was rated fair. This is generally a commercially acceptable minimum level of emulsion stability. Where cream amounted to greater than 4% of total volume, emulsion stability was rated poor.

Examples 1–5

Compositions of Examples 1, 3, 4 and 5 of the invention were prepared using a high shear homogenizer, and the composition of Example 2 of the invention was prepared using a low shear mixer. It has been found preferable to utilize a low shear mixer to manufacture a suspension concentrate composition of the invention if possible.

Compositions of Examples 1, 2, 3 and 4 used an unmilled solid pesticide, and the composition of Example 5 used a milled solid pesticide.

The compositions of Examples 1–5 were prepared using a two-phase addition method. During a first phase, the solid pesticide was added to the liquid pesticide with appropriate and adequate mixing to form a Phase I mixture. During a second phase, surfactants were first blended together in any order, and silica was subsequently added to form a Phase II mixture. The Phase I and Phase II mixtures were then added together with adequate mixing to form the final mixture.

Ingredients and amounts thereof used in preparing compositions of Examples 1–5, and physical properties of these compositions, are shown in Table 1.

TABLE 1

Compositions and properties of Examples 1–5 (% by weight)

| Example | 1 | 2 | 3 | 4 | 5 |
|---|---|---|---|---|---|
| solid pesticide: glyphosate | 24.1 | 23.9 | 24.1 | 24.1 | 24.1 |
| Liquid pesticide: acetochlor | 50.9 | 50.7 | 50.9 | 50.9 | 50.9 |

TABLE 1-continued

Compositions and properties of Examples 1–5 (% by weight)

| Example | 1 | 2 | 3 | 4 | 5 |
|---|---|---|---|---|---|
| surfactant: Witconate ® 1298 HA[1] | 1.3 | 1.3 | 1.3 | 1.3 | 1.3 |
| surfactant: Witcamine ® TAM-105[2] | 11.4 | 11.4 | 11.4 | 11.4 | 11.4 |
| surfactant: Witconol ® SN-120[3] | 2.0 | 2.0 | 2.0 | 2.0 | 2.0 |
| surfactant: Sponto ® AL69-66[4] | 2.0 | 2.0 | 2.0 | 2.0 | 2.0 |
| surfactant: Witconol ® NS-500 LQ[5] | 4.6 | 3.3 | 4.3 | 4.7 | 4.6 |
| surfactant: Witconate ® P-1059[6] | 1.8 | 3.4 | 2.0 | 2.8 | 1.8 |
| suspension aid: Hi-Sil ® T-152[7] | 1.9 | — | 2.0 | — | 1.9 |
| suspension aid: Aerosil ® 200[8] | — | 2.0 | — | 0.8 | — |
| total weight % | 100.0 | 100.0 | 100.0 | 100.0 | 100.0 |
| viscosity at 25° C. (cPs), 12 rpm | 1800 | 1700 | 3500 | 4360 | 4960 |
| physical stability at ambient temperature (clear oil layer as % of total volume) | <2 (2 wk) | <2 (2 wk) | <5 (4 wk) | <2 (2 wk) | (3 wk) |
| Bloom | fair | fair | fair | fair | fair |
| emulsion stability | exc. | exc. | exc. | exc. | exc. |

[1]sulfonic acid surfactant
[2]ethoxylated tallowamine surfactant
[3]ethoxylated alcohol surfactant
[4]ethoxylated sorbitol tallate surfactant
[5]butanol EO/PO block copolymer surfactant
[6]isopropylammonium dodecylbenzene sulfonate surfactant
[7]precipitated silica
[8]fumed silica As can be seen in Table 1, the compositions of Examples 1–5 exhibited satisfactory physical stability as concentrates, and upon dilution exhibited satisfactory bloom and excellent emulsion stability.

Example 6

The composition of Example 6 (Table 2) was prepared using a high shear homogenizer. This composition illustrates that a small amount of an inert solvent suitable for use in assay adjustment can be present in the composition without adversely affecting the physical properties.

TABLE 2

Composition and properties of Example 6 (% by weight)

| Example | 6 |
|---|---|
| solid pesticide: glyphosate acid | 25.0 |
| Liquid pesticide: 2,4-D diisooctyl ester | 50.0 |
| Witconate ® 1298 HA[1] | 7.6 |
| alkylamine | 1.4 |
| 2-ethylhexanol | 0.6 |
| Witconol ® CO-360[2] | 2.4 |
| Witconol ® CO-550[3] | 2.4 |
| Witconol ® NS-500 LQ[4] | 4.9 |
| Cyclosol<® 150[5] | 5.0 |
| Aerosil ® 200[6] | 0.7 |
| Total weight % | 100.0 |
| viscosity at 25° C. (cPs), 12 rpm | 2910 |
| physical stability at ambient temperature | stable |

TABLE 2-continued

Composition and properties of Example 6 (% by weight)

| Example | 6 |
|---|---|
| bloom | satisfactory |
| emulsion stability | satisfactory |

[1]sulfonic acid surfactant
[2-3]ethoxylated castor oil surfactants
[4]butanol EO/PO block copolymer surfactant
[5]aromatic hydrocarbon solvent
[6]fumed silica

Examples 7–14

The compositions of Examples 7–14 were prepared by the following procedure. First, the liquid ingredients were added in any order and mixed in a wet media mill with shearing, e.g., a Waring blender. The solid ingredients (solid particulate pesticide and silica) were then added with further mixing to form a blended mixture. This blended mixture, in an amount of 350 ml, was then transferred to an Eiger mill, where it was recirculated for about 30 minutes at a shaft speed of 1000 rpm.

Ingredients and amounts thereof used in preparing compositions of Examples 7–10 are shown in Table 3. Ingredients and amounts thereof used in preparing compositions of Examples 11–14 are shown in Table 4.

TABLE 3

Compositions of Examples 7–10 (% by weight)

| Example | 7 | 8 | 9 | 10 |
|---|---|---|---|---|
| Solid pesticide: glyphosate ammonium salt[1] | 26.4 | 26.4 | 26.4 | 26.4 |
| liquid pesticide: acetochlor | 56.4 | 56.3 | 56.3 | 56.3 |
| alkylphenylether sulfate, tallowamine EO salt | 4.7 | 4.7 | 4.7 | 4.5 |
| nonionic surfactant blend[2] | 2.8 | 2.8 | 2.7 | 3.0 |
| ethoxylated tallowamine surfactant | 3.9 | 9.2 | 7.7 | — |
| ethoxylated alkyletheramine surfactant[3] | — | — | — | 3.8 |
| Aromatic 200 solvent of Exxon | 4.7 | 0.1 | 1.7 | 5.5 |
| silica suspension aid: Aerosil ® 200 | 1.1 | 0.5 | 0.5 | 0.5 |
| total weight % | 100.0 | 100.0 | 100.0 | 100.0 |

[1]87.5% glyphosate acid equivalent
[2]blend of sorbitol tallate and butanol EO/PO block copolymer
[3]surfactant of formula

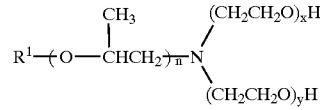

where $R^1$ is $C_{12-15}$ alkyl, n is 2 and x+y is 5, as disclosed in U.S. Pat. No. 5,750,468, incorporated herein by reference

TABLE 4

Compositions of Examples 11–14 (% by weight)

| Example | 11 | 12 | 13 | 14 |
|---|---|---|---|---|
| solid pesticide: glyphosate ammonium salt[1] | 26.4 | 26.4 | 26.4 | 26.4 |
| liquid pesticide: acetochlor | 56.3 | 56.3 | 56.3 | 56.3 |
| alkylphenylether sulfate, tallowamine EO salt | 4.4 | 4.4 | 3.7 | 3.7 |
| nonionic surfactant blend[2] | 3.0 | 3.0 | 2.5 | 2.5 |
| ethoxylated tallowamine surfactant | — | — | 9.2 | 7.7 |

TABLE 4-continued

Compositions of Examples 11–14 (% by weight)

| Example | 11 | 12 | 13 | 14 |
|---|---|---|---|---|
| ethoxylated alkyletheramine surfactant[3] | 3.1 | 4.6 | — | — |
| Aromatic 200 solvent of Exxon | 6.3 | 4.8 | 1.6 | 3.1 |
| Aerosil ® 200 | 0.5 | 0.5 | 0.3 | 0.3 |
| total weight % | 100.0 | 100.0 | 100.0 | 100.0 | footnotes to Table 3

Examples 15–20

The compositions of Examples 15–20 were prepared by the following procedure. The ingredients were added in the following order and mixed in a Waring blender for the times indicated: acetochlor, ether sulfate tallowamine EO salt and nonionic surfactant blend (5 minutes); Aromatic 200; dispersing agent (5 minutes); ethoxylated tallowamine surfactant (5 minutes); solid particulate ammonium glyphosate (10 minutes); hydrophobic silica (5 minutes); hydrophilic silica (10 minutes).

Ingredients and amounts thereof used in preparing compositions of Examples 15–20 are shown in Table 5.

TABLE 5

Compositions of Examples 15–20 (% by weight)

| Example | 15 | 16 | 17 | 18 | 19 | 20 |
|---|---|---|---|---|---|---|
| glyphosate ammonium salt[1] | 24.6 | 26.3 | 26.3 | 26.5 | 26.5 | 26.5 |
| acetochlor | 52.8 | 56.6 | 56.6 | 56.6 | 56.6 | 56.6 |
| ether sulfate, tallowamine EO salt[2] | 2.8 | 3.7 | 3.0 | 3.7 | 4.0 | 2.5 |
| Nonionic surfactant blend[3] | 1.9 | 2.4 | 2.0 | 2.4 | 3.0 | 1.7 |
| ethoxylated tallowamine surfactant | 8.0 | 8.0 | 8.0 | 8.0 | 8.0 | 8.0 |
| Aromatic 200 solvent of Exxon | 7.4 | 0.5 | 1.6 | 1.9 | 0.5 | 2.2 |
| hydrophobic silica[4] | 0.25 | — | 0.25 | — | — | 0.1 |
| hydrophilic silica[5] | 0.25 | 0.5 | 0.25 | — | 0.5 | 0.4 |
| polyoxyethylene (3) $C_{11}$ alcohol[6] | 2.0 | 2.0 | 2.0 | — | — | — |
| polyoxyethylene (5) $C_{11}$ alcohol[7] | — | — | — | 0.9 | — | — |
| polyoxyethylene (7) $C_{11}$ alcohol[8] | — | — | — | — | 0.9 | — |
| poloxyethylene (12) $C_{12-15}$ alcohol[9] | — | — | 2.0 | — | — | — |
| total weight % | 100.0 | 100.0 | 100.0 | 100.0 | 100.0 | 100.0 |

[1]87.5% glyphosate acid equivalent
[2]alkylphenylether sulfate, tallowamine EO salt
[3]blend of sorbitol tallate and butanol EO/PO block copolymer
[4]Aerosil ™ R-972 of Degussa
[5]Aerosil ™ 200 of Degussa
[6]Neodol ™ 1–3 of Shell, dispersing agent
[7]Tornadol ™ 1–5 of Tornah, dispersing agent
[8]Tornadol ™ 1–7 of Tornah, dispersing agent
[9]Tornadol ™ 25–12 of Tornah, dispersing agent Viscosity of the compositions of Examples 15–17 was measured at 25° C. and 10° C. Results are shown in Table 6.

TABLE 6

Viscosity (cPs) of compositions of Examples 15–17

| | Example 15 | Example 16 | Example 17 |
|---|---|---|---|
| 25° C. | 235 | 369 | 343 |
| 10° C. | 640 | 1059 | 998 |

Note that the viscosity measurements in Table 6 above were made with a Haake RV20 viscometer at a shear rate of 45 sec$^{-1}$ and are not directly comparable with viscosities measured using a Brookfield viscometer as described elsewhere herein.

What is claimed is:

1. An emulsifiable pesticidal suspension concentrate composition comprising
   (a) a pesticidally effective amount of a liquid pesticide of low solubility in water;
   (b) a pesticidally effective amount of a solid salt-forming particulate pesticide, dispersed in the liquid pesticide and chemically compatible therewith;
   (c) a stabilizing amount of a suspension aid;
   (d) an emulsifying agent in an amount sufficient to emulsify the concentrate composition in a suitable volume of water to form a dilute sprayable composition; and
   (e) an assay adjusting amount of an inert liquid in which the liquid pesticide is soluble or miscible, said assay adjusting amount not exceeding 10% by weight of the composition;
the concentrate composition being substantially non-aqueous.

2. The composition of claim 1 comprising not more than 5% by weight of the inert liquid.

3. The composition of claim 1 having a total pesticide concentration of about 40% to about 97% by weight.

4. The composition of claim 1 having a total pesticide concentration of about 60% to about 90% by weight.

5. The composition of claim 1 having a weight ratio of total solid pesticide, expressed where appropriate as acid equivalent, to total liquid pesticide of about 1:9 to about 2:1.

6. The composition of claim 1 wherein the solid salt-forming particulate pesticide is selected from the group consisting of aryloxyphenoxypropionates, benazolin, bipyridyls, carfentrazone, difenzoquat, flumiclorac, glufosinate, glyphosate, imidazolinones, phenoxyalkanoic acids, pyridinecarboxylic acids, quinolinecarboxylic acids, acifluorfen and fluoroglycofen; said pesticide being present in the composition in acid or base form, or in the form of an agriculturally acceptable salt thereof.

7. The composition of claim 6 wherein the solid salt-forming pesticide is selected from the group consisting of aryloxyphenoxypropionates, bipyridyls, glufosinate, glyphosate and phenoxyalkanoic acids.

8. The composition of claim 7 wherein the solid particulate pesticide is selected from glufosinate and glyphosate.

9. The composition of claim 8 wherein the solid particulate pesticide is selected from glyphosate acid and the ammonium and sodium salts of glyphosate.

10. The composition of claim 8 that comprises one or more surfactants that enhance glyphosate herbicidal activity in plants, said surfactants being selected from alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene -methyl alkylammonium salts, polyoxyethylene -methyl alkyletherammonium salts, alkyldimethylamine oxides, polyoxyethylene alkylamine oxides, polyoxyethylene alkyletheramine oxides, alkylbetaines and alkylamidopropylamines, where the average number of oxyethylene units, if present, per surfactant molecule is no greater than about 50, and the average number of glucose units, if present, per surfactant molecule is no greater than about 2.

11. The composition of claim 8 that comprises
  (a) at least one liquid pesticide;
  (b) about 5% to about 15% by weight of at least one alkylamine ethoxylate surfactant;
  (c) about 1% to about 10% by weight of at least one EO/PO block copolymer;
  (d) about 1% to about 10% of at least one additional nonionic surfactant;
  (e) about 1% to about 10% of at least one sulfonic acid or sulfonate surfactant; and
  (f) about 0.5% to about 5% by weight of at least one silica; said composition having a total pesticide concentration of about 65% to about 85% by weight, and having a weight ratio of glyphosate, expressed as acid equivalent, to said liquid pesticide of about 1:5 to about 1:1.

12. The composition of claim 1 wherein the suspension aid comprises a silica.

13. The composition of claim 12 wherein said silica is a hydrophilic fumed or precipitated silica.

14. The composition of claim 12 wherein said silica has a BET surface area of about 100 to about 300 $m^2/g$ and a bulk density of about 10 to about 70 g/l.

15. The composition of claim 12 wherein said silica is present in an amount of about 0.5% to about 5% by weight of the composition.

16. The composition of claim 1 wherein the emulsifying agent comprises one or more surfactants selected from block copolymers of ethylene oxide and propylene oxide or butylene oxide, alkylaryl alkoxylates, tertiary ($C_{8-22}$ alkyl)amine and ($C_{8-22}$ alkyl)etheramine alkoxylates, quaternary ($C_{8-22}$ alkyl)ammonium and ($C_{8-22}$ alkyl)etherammonium salts and alkoxylates thereof, fatty acid alkoxylate esters, fatty alcohol alkoxylates, alkylsulfonates, alkylbenzene and alkylnaphthalene sulfonates, sulfated fatty alcohols and alkylether sulfates, sulfated amines and acid amides, long-chain acid esters of sodium isethionate, esters of sodium sulfosuccinate, sulfated and sulfonated fatty acid esters, petroleum sulfonates, N-acyl sarcosinates, alkyl polyglycosides, sorbitan esters, and phosphate esters of fatty alcohols and fatty alcohol alkoxylates.

17. The composition of claim 1 wherein the liquid pesticide is a herbicide selected from aryloxyphenoxy herbicides, chloroacetamides, cyclohexanediones and esters of phenoxy herbicides.

18. An emulsifiable pesticidal suspension concentrate composition comprising
  (a) a pesticidally effective amount of a liquid chloroacetamide pesticide;
  (b) a pesticidally effective amount of a solid salt-forming particulate pesticide, dispersed in the liquid pesticide and chemically compatible therewith;
  (c) a stabilizing amount of a suspension aid;
  (d) an emulsifying agent in an amount sufficient to emulsify the concentrate composition in a suitable volume of water to form a dilute sprayable composition; and
  (e) an assay adjusting amount of an inert liquid in which the liquid pesticide is soluble or miscible, said assay adjusting amount not exceeding 10% by weight of the composition;

the concentrate composition being substantially non-aqueous.

19. The composition of claim 18 wherein the emulsifying agent comprises one or more surfactants selected from block copolymers of ethylene oxide and propylene oxide or butylene oxide, alkylaryl alkoxylates, tertiary ($C_{8-22}$ alkyl)amine and ($C_{8-22}$ alkyl)etheramine alkoxylates, quaternary ($C_{8-22}$ alkyl)ammonium and ($C_{8-22}$ alkyl)etherammonium salts and alkoxylates thereof, fatty acid alkoxylate esters, fatty alcohol alkoxylates, alkylsulfonates, alkylbenzene and alkyl naphthalene sulfonates, sulfated fatty alcohols and alkylether sulfates, sulfated amines and acid amides, long-chain acid esters of sodium isethionate, esters of sodium sulfosuccinate, sulfated and sulfonated fatty acid esters, petroleum sulfonates, N-acyl sarcosinates, alkyl polyglycosides, sorbitan esters, and phosphate esters of fatty alcohols and fatty alcohol alkoxylates.

20. The composition of claim 18 compnrising not more than 5% by weight of the inert liquid.

21. The composition of claim 18 having a total pesticide concentration of about 40% to about 97% by weight.

22. The composition of claim 18 having a total pesticide concentration of about 60% to about 90% by weight.

23. The composition of claim 18 having a weight ratio of total solid pesticide, expressed where appropriate as acid equivalent, to total liquid pesticide of about 1:9 to about 2:1.

24. The composition of claim 18 wherein the chloroacetamide pesticide is selected from acetochlor and metolachlor.

25. The composition of claim 18 wherein the solid salt-forming particulate pesticide is selected from the group consisting of aryloxyphenoxypropionates, benazolin, bipyridyls, carfentrazone, difenzoquat, flumiclorac, glufosinate, glyphosate, imidazolinones, phenoxyalkanoic acids, pyridinecarboxylic acids, quinolinecarboxylic acids, acifluorfen and fluoroglycofen; said pesticide being present in the composition in acid or base form, or in the form of an agriculturally acceptable salt thereof.

26. The composition of claim 25 wherein the solid particulate pesticide is selected from glufosinate and glyphosate.

27. The composition of claim 26 wherein the solid particulate pesticide is selected from glyphosate acid and the ammonium and sodium salts of glyphosate.

28. The composition of claim 19 wherein the suspension aid comprises a silica.

29. The composition of claim 28 wherein said silica is a hydrophilic fumed or precipitated silica.

30. The composition of claim 28 wherein said silica has a BET surface area of about 100 to about 300 $m^2/g$ and a bulk density of about 10 to about 70 g/l.

31. The composition of claim 28 wherein said silica is present in an amount of about 0.5% to about 5% by weight of the composition.

32. The composition of claim 25 wherein the solid salt-forming pesticide is selected from the group consisting of aryloxyphenoxypropionates, bipyridyls, glufosinate, glyphosate and phenoxyalkanoic acids.

33. The composition of claim 26 that comprises one or more surfactants that enhance glyphosate herbicidal activity in plants, said surfactants being selected from alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene -methyl alkylammonium salts, polyoxyethylene -methyl alkyletherammonium salts, alkyldimethylamine oxides, polyoxyethylene alkylamine oxides, polyoxyethylene alkyletheramine oxides, alkylbetaines and alkylamidopropylamines, where the average number of oxyethylene units, if present, per surfactant molecule is no greater than about 50, and the average number of glucose units, if present, per surfactant molecule is no greater than about 2.

34. The composition of claim 26 that comprises
    (a) at least one liquid chloroacetamide pesticide;
    (b) about 5% to about 15% by weight of at least one alkylamine ethoxylate surfactant;
    (c) about 1% to about 10% by weight of at least one EO/PO block copolymer;
    (d) about 1% to about 10% of at least one additional nonionic surfactant;
    (e) about 1% to about 10% of at least one sulfonic acid or sulfonate surfactant; and
    (f) about 0.5% to about 5% by weight of at least one silica; said composition having a total pesticide concentration of about 65% to about 85% by weight, and having a weight ratio of glyphosate, expressed as acid equivalent, to said liquid pesticide of about 1:5 to about 1:1.

* * * * *